(12) United States Patent
Graether

(10) Patent No.: US 7,922,329 B1
(45) Date of Patent: Apr. 12, 2011

(54) SLIT-LAMP PHOTO ASSEMBLY

(75) Inventor: John M. Graether, Marshalltown, IA (US)

(73) Assignee: Oculocam, LLC, Marshalltown, IA (US)

( * ) Notice: Subject to any disclaimer, the term of this patent is extended or adjusted under 35 U.S.C. 154(b) by 0 days.

(21) Appl. No.: 12/625,911

(22) Filed: Nov. 25, 2009

(51) Int. Cl.
*A61B 3/10* (2006.01)
*A61B 3/00* (2006.01)

(52) U.S. Cl. .................. 351/205; 351/221; 351/246

(58) Field of Classification Search .......... 351/205–206, 351/210, 221, 244–246, 200, 214; 180/116–117, 180/125, 127, 164, 209; 280/43, 43.14, 43.17, 280/43.23, 43.24
See application file for complete search history.

(56) References Cited

U.S. PATENT DOCUMENTS

| | | | |
|---|---|---|---|
| 3,484,165 A * | 12/1969 | Denner | 355/67 |
| 3,944,342 A | 3/1976 | Martinez | |
| 4,331,392 A | 5/1982 | Sato | |
| 4,411,502 A | 10/1983 | Lang et al. | |
| 4,504,129 A | 3/1985 | Van Iderstine | |
| 4,767,204 A | 8/1988 | Blaha | |
| 4,779,973 A * | 10/1988 | Miller et al. | 351/212 |
| 5,870,167 A | 2/1999 | Knopp et al. | |
| 5,877,837 A * | 3/1999 | Hayes | 351/44 |
| 5,886,768 A | 3/1999 | Knopp et al. | |
| 6,361,167 B1 | 3/2002 | Su et al. | |
| 7,083,281 B2 | 8/2006 | Yogesan et al. | |
| 2005/0041207 A1 * | 2/2005 | Miller et al. | 351/200 |

* cited by examiner

*Primary Examiner* — Ricky L Mack
*Assistant Examiner* — Dawayne A Pinkney

(57) ABSTRACT

A slit-lamp assembly that has a pivoting arm that is removably connected to a vertical column associated with a frame. The pivoting arm supports a plate spindle assembly that supports a camera wherein the plate spindle assembly includes a bracket that secures a digital camera thereto and a light assembly thereto so that the lens of the camera is disposed through a circular opening of the light assembly.

21 Claims, 4 Drawing Sheets

SLIT-LAMP PHOTO ASSEMBLY

BACKGROUND OF THE INVENTION

This invention relates to a slit-lamp photo assembly used in association with eye care. More specifically, this invention relates to a slit-lamp assembly that utilizes an attachment with a camera.

The slit-lamp is the basic examination tool of an eye practitioner (the ophthalmologist, optometrist and their staffs). A typical slit-lamp consists of (1) a horizontal platform or table with a vertical frame attached containing an adjustable chin and forehead support for the patient's head where the platform is positioned in front of the seated patient; (2) on the platform is a movable carriage mounted on a track controlled by a joystick handle to move the carriage back and forth; (3) mounted on the carriage is an adjustable vertical column to which two pivoting arms are attached. One arm carries the binocular microscope through which the observer can see the magnified eye. The other arm supports a vertically oriented light source that provides an adjustable slit beam that is converted to a horizontal beam by a mirror and projected onto the patient's eye.

While the slit-lamp is sufficient for eye practitioners in order to examine eyes, problems still remain. Specifically, a desire to take snapshots or closer examination utilizing some type of camera device was desired. As a result, photo slit-lamps have been provided.

A photo slit-lamp is a modification of the basic slit-lamp in which a camera is integrated into the microscope usually through a prism or partially silvered mirror to allow a monocular photo to be taken of the image observed through the oculars. The photo slit-lamp usually has an accessory external light source and is now usually integrated with a computer system to process the digital image.

While the photo slit-lamp allows a practitioner to take images of an eye, many problems still remain. First, the modification including integrating the camera into the microscope limits the use of the slit-lamp. In addition, photo slit-lamps are very expensive and occupy dedicated space to which a patient must be transported for the photography. In addition, photo slit-lamps are often difficult and time consuming to use and often require a specially trained photographer for best results.

Therefore, a principal object of the present invention is to provide a slit-lamp assembly that utilizes a camera that is cost efficient.

Yet another object of the present invention is to provide a slit-lamp assembly that utilizes a camera that is adaptable to existing slit-lamp assemblies.

These and other objects, features, and advantages will become apparent from the specification and claims.

BRIEF SUMMARY OF THE INVENTION

A slit-lamp photo assembly that has a frame that is attached to a platform wherein the frame contains a head support for a patient. A carriage is movably connected to the platform and has a vertical column. A first pivoting arm is rotatably connected to the vertical column and supports a binocular microscope. A second pivoting arm is also rotatably connected to the vertical column and supports a vertically oriented light source that provides an adjustable slit-beam.

In addition, a third pivoting arm is provided that is removably connected to the vertical column by a spindle plate and supports a plate spindle assembly and supports a camera. The plate spindle assembly includes a base plate that receives an adjustable arm therein and receives a bracket on which the camera is mounted. In addition, a light assembly is secured to the bracket so that the light assembly surrounds the lens of the camera.

DETAILED DESCRIPTION OF THE PREFERRED EMBODIMENT

Figure 1:
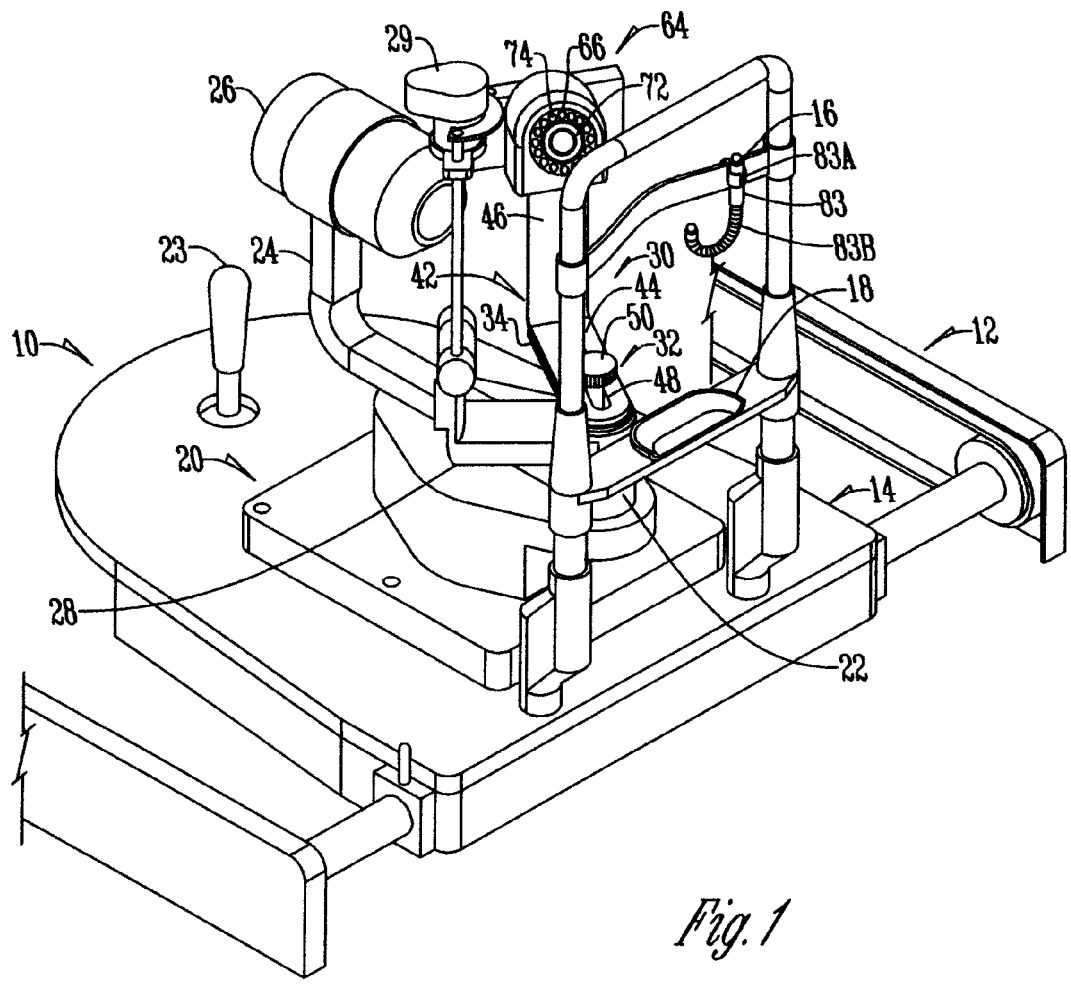
FIG. 1 is a side perspective view of a slit-lamp photo assembly.
Figure 1A:
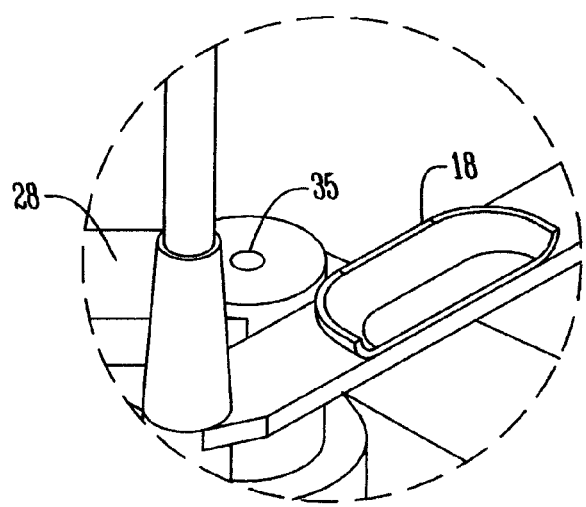
FIG. 1A is a partial perspective view of a slit-lamp photo assembly.

FIG. 1 shows a slit-lamp photo assembly 10. The slit-lamp assembly 10 has a frame 12 that is attached to a platform 14 that has a head support 16 and chin support 18 for a patient as is known in the art. Similarly, a carriage 20 is movably connected to the platform 14 and has a vertical column 22. The carriage 20 is movable on a track that is controlled by a joystick 23 to move back and forth as is known in the art.

The adjustable vertical column 22 has a first pivoting arm 24 that is rotatably connected to the vertical column 22 and supports a binocular microscope 26. A second pivoting arm 28 is also rotatably connected to the vertical column 22 and supports a vertically oriented light source 29 that provides an adjustable slit beam.

Additionally provided is a third pivoting arm 30 that is removably connected to the vertical column 22 by a spindle plate assembly 32. Specifically, the third pivoting arm 30 may be attached to any generic vertical column have a central opening 35 typically used in a known slit-lamp assembly. In one embodiment the third pivoting arm is removably connected to the vertical column.

The plate spindle assembly 32 has a plate 34 that has a vertical shaft or spindle 36 that both removably and rotatably connects the plate 34 to the vertical column 22. The plate 34 additionally has recessed area 38 wherein a threaded opening is disposed through the plate 34 in the recessed area 38.

Figure 2:
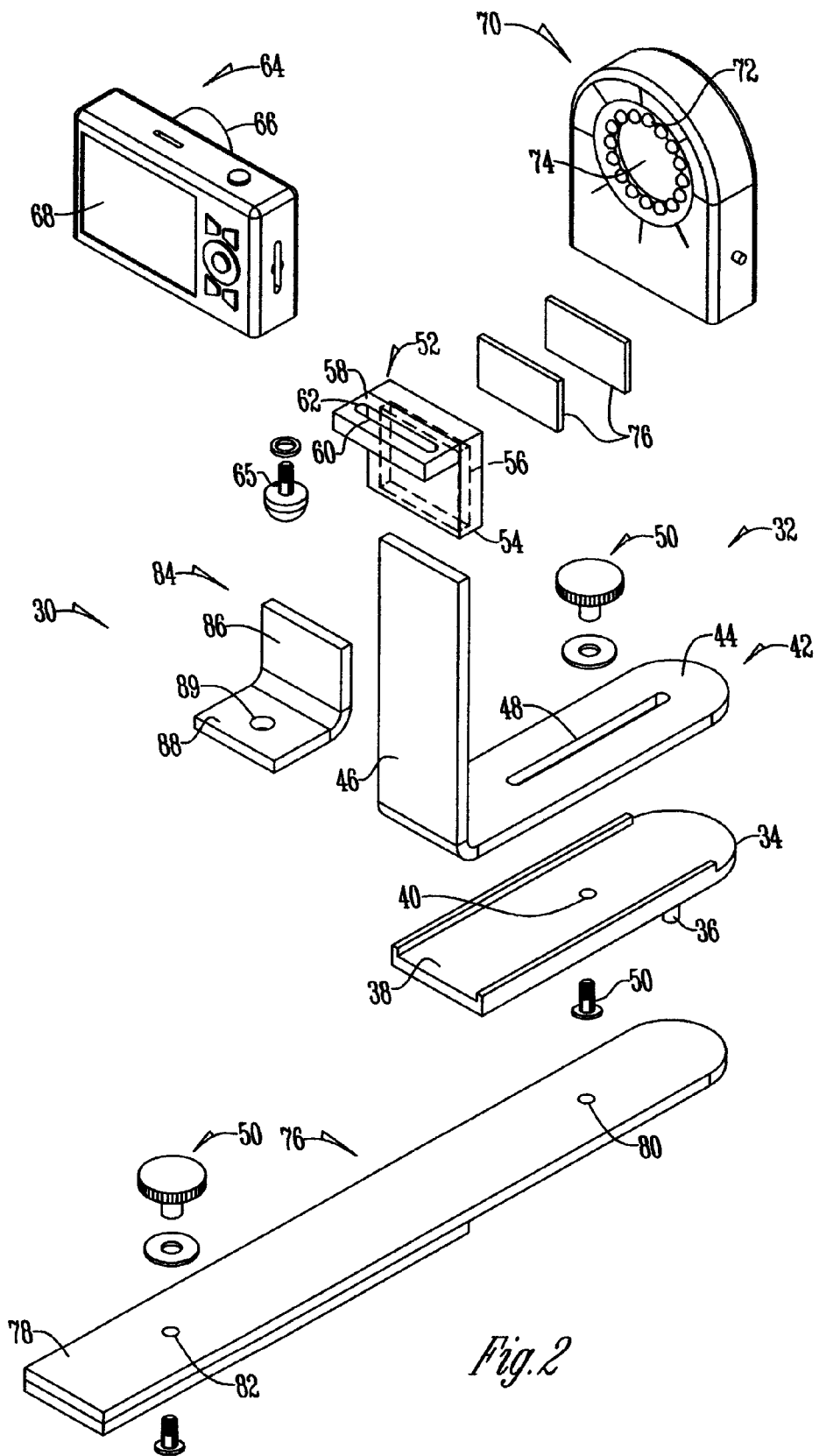
FIG. 2 is an exploded view of a plate spindle assembly of a slit-lamp photo assembly.

The plate spindle assembly 32 additionally includes a camera support arm 42 that has a horizontal portion 44 that is received within the recessed area 38 of the spindle base 34 and additionally the camera support arm 42 has a vertical portion 46 extending vertically from the horizontal portion 44. The horizontal portion 44 has an elongated slot 48 so that a fastening device 50 such as a fluted knob used in combination with a flat head screw as shown in FIG. 2 can be used to slidably and adjustably secure the arm 42 to the plate 34. Thus, when the horizontal portion 44 of the arm 42 is within the recessed area 38 of the plate 34 the elongated slot 48 aligns with the opening 40 of the plate 34 so that the arm 42 may be adjustably slid and secured in place as desired.

The plate spindle assembly 32 additionally has a bracket 52 that in a preferred embodiment is an injected molded bracket. The bracket 52 has a vertical portion 54 that contains a cavity 56 therein that receives the vertical portion 46 of the arm 42 allowing the bracket 52 to slide onto and be removably connected to the arm 42. Extending from the vertical portion 54 is a horizontal portion 58 that has an elongated slot 60 that is surrounded by an arcuate recessed area 62. The elongated slot 60 and recessed area 62 are presented to provide an adjustable attachment to a digital camera 64. Specifically, as is known in the art different types of cameras have different mounting points and thus the elongated slot allows for a fastening member 65 to be utilized in association with the camera 64 to mount the camera regardless of the position of the tripod socket on the bottom of the camera 64. In a preferred embodiment the fastening member 65 is a tripod screw.

Camera 64 is any digital camera known in the art including but not limited to a Canon®, Nikon®, Sony® and the like. In general, the camera has a camera lens 66 extending from one side of the camera and a liquid crystal display (LCD) screen 68 at the other side of the camera as is known in the art.

Additionally secured to the bracket 52 is a light assembly 70 that in a preferred embodiment is a compact LED ring light that is battery operated as shown in FIG. 2. Thus, the light assembly 70 has a light ring 72 surrounding an opening 74 wherein the light assembly 70 is adjustably secured to the bracket 52 using dual lock tape 76. In a preferred embodiment the dual lock tape 76 is 3M™ Dual-Lock™ tape. When secured to the bracket 52 the light assembly 70 is positioned so that the lens 66 of the camera 64 is disposed through the opening 74 of the light assembly 70. Together when the light assembly 70 is secured to the bracket 52 and positioned to that the lens 66 of the camera is disposed through the opening 74 of the light assembly a camera light assembly (52, 64 and 70) is formed.

The plate spindle assembly 32 optionally can also use an extension arm 76. The extension arm 76 has an elongated body 78 that is longer than the plate 34 wherein the body has two spaced apart openings 80 and 82. Thus, the extension arm 76 can be received within the plate 34 so that an opening 80 aligns with opening 40 such that fastening member 50 can be disposed through both openings 80 and 40 to provide a connection on the camera support arm 42. Alternatively, the arm 42 can be moved to align the elongated slot 48 with opening 82 such that the arm 42 is spaced apart and extended away from the plate 34 and thus the vertical column 22. Thus the extension arm 76 allows the camera 64 to be used for video photography.

As an option, a battery operated LED light 83 can be clipped with clip 83A on the head support 16 as an accessory external light. This single LED light has a flexible extension arm 83B that allows the light 83 to be positioned close to the eye to be photographed. When using the LED light 83 the vertically oriented light source 29 continues to produce a slit beam such that the slit-lamp remains in operation and can be included in the photograph when desired.

Figure 3:
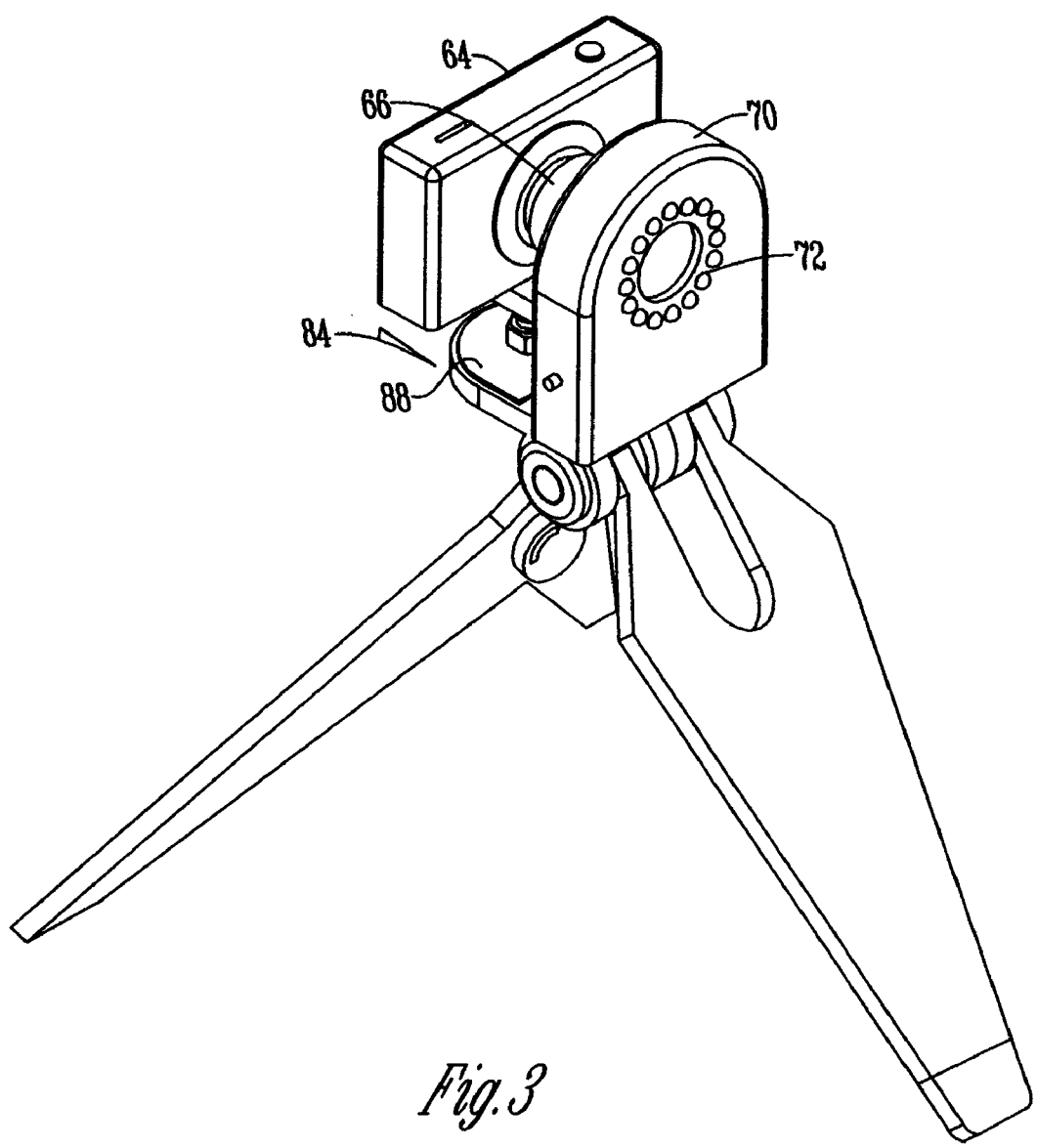
FIG. 3 is a perspective view of an alternative embodiment of a camera light assembly.

In an alternative embodiment as shown in FIG. 3 a tripod mount bracket 84 replaces the plate 34 and camera support arm 42 within the plate spindle assembly 32. Thus, the bracket 52 slides on a vertical portion 86 of the tripod mount L-shaped bracket 84 and a horizontal portion 88 is presented to secure the bracket 84 accordingly. The horizontal portion 88 has a threaded hole 89 for attachment to a base. Therefore, the camera 64 and light assembly 70 can still be attached to the bracket 52 and an effective tripod attachment is presented.

Figure 4:
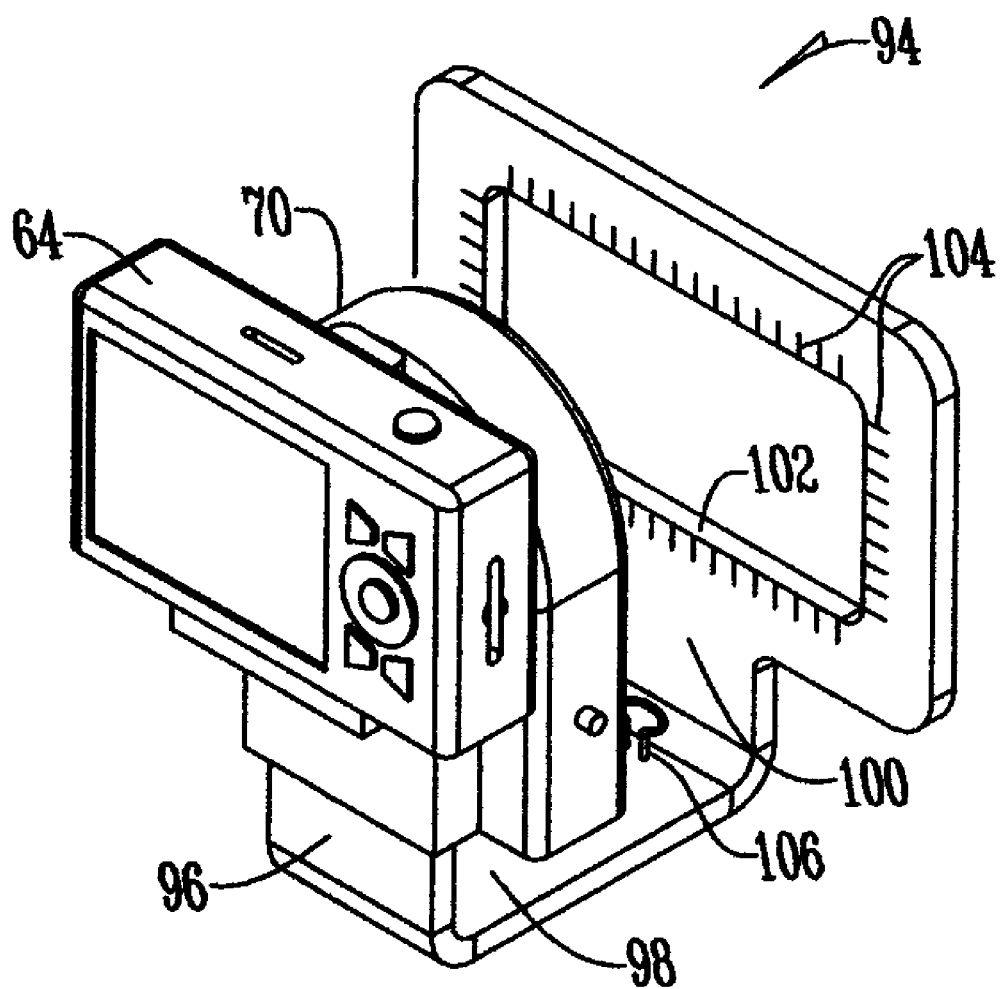
FIG. 4 is a perspective view of an alternative embodiment of a camera light assembly.

In another alternative embodiment as shown in FIG. 4 a photo template system 94 can be attached to the camera light assembly (52, 64 and 70). The photo template system 94 has an upwardly extending flange 96 that is received within the cavity 56 of the bracket 52. Extending generally perpendicular to the flange 96 is an extension 98. Extending generally perpendicular to the extension 98 and parallel to the flange 96 is a template 100 that has an opening 102 therein. Surrounding the opening 102 are measurement indicia 104 such as marks indicating a distance in mm. In a preferred embodiment the indicia 104 provides a mm scale permanently applied on all sides of the opening 102. A clip 106 is attached to the photo template system 94 to allow a small paper sheet or card to be placed over the interior portion of the template 100 for patient identification, specific information to be included with the photo, or the like. In the embodiment of FIG. 4 the clip 106 is secured to the extension 98 and biases against the template 100. In a preferred embodiment the photo template system 94 comprises a plastic overlay fused to an aluminum frame with a mm scale on a white background.

In operation, the third pivoting arm 30 is secured to the vertical column 22. The camera 64 and light assembly 70 are then secured to the bracket 52 of the plate spindle assembly 32 and examination of the eye can be accomplished. By utilizing an LED ring light as the light assembly 70 a circular image, or Purkinje image can be presented on the cornea that can be used diagnostically. Alternatively, when a video is desired the extension bracket 76 can be used to provide the desired distance.

Thus presented is a slit-lamp photo assembly 10 that adds a third pivoting arm 30 to an existing slit-lamp's vertical column 22 that allows the substitution of a small digital camera 64 with an LCD viewing screen 68 for the slit-lamp microscope 26 while the microscope is placed to the side. In addition to the camera 64 the third pivoting arm 30 supports a light assembly 70 that can be an LED ring light that surrounds the lens 66 of the camera 64 and provides an additional light that can be imaged on the patient's cornea as a ring. This ring not only provides general illumination, but also the circular image, or Purkinje image on the cornea can be used diagnostically. Therefore, this device is a slit-lamp camera system that allows the operator to observe the eye through the LCD screen 68 on the back of the camera 64 so that he/she can observe the actual image being projected onto the camera's sensor including the slit beam.

An additional advantage includes that the assembly can be completely battery operated and easily attached to any Haag-Streit type of slit-lamp. The unit is installed by simply placing the plate 34 in the hole in the slit-lamps vertical column 22 and attaching the accessory light 90 (if needed) to the head support 16 with its attached pocket clip 92. Thus, the assembly 10 can be taken to the patient already seated at the slit-lamp and does not require a dedicated slit-lamp or additional exam space. Additionally, the cost of the third pivoting arm 30 and camera light assembly (52, 64 and 70) is a small fraction of a dedicated photo slit-lamp. In addition the assembly 10 can expand the photo possibilities beyond a dedicated photo slit-lamp by adding the light ring 72 and by allowing a broader view of the subject (full face image) and a stimulus view of actual photo image as it is created.

Specifically, the plate spindle assembly 32 allows instantaneous attachment of the camera 64 to the unmodified slit-lamp. The plate spindle assembly 32 also permits the camera 64 and integrated light assembly 70 that typically is a LED ring light to be positioned relative to the slit beam and the patient via the adjustable arm 42 by which the camera 64 is attached. In addition, this plate spindle assembly 32 accommodates an extension arm 76 that allows the camera 64 to be used for video photography that can also employ all three modes of lighting (the ring light via light assembly 70, the slit beam via vertical oriented light source 29 and the external single LED via LED light 90).

The bracket 52 meanwhile connects the camera 64 and the light assembly 70 and joins them to the arm 42 that attaches the camera 64 to the slit-lamp via a plate spindle assembly 32. This bracket 52 has a slot 60 that allows adjustment for the various tripod socket locations on the camera 64 and attaches the light assembly 70 via the dual lock tape system 76. This attachment 76 permits easy placement of the light ring 72 coexcentric with the camera's lens 66 by merely aligning the light and pushing them together. The bracket 52 therefore accommodates a variety of small cameras and does not require a lens 66 with a threaded mount to attach the light assembly 70. Consequently, the system 10 takes full advantage of the properties of a small, high resolution, camera 64 that has many automatic features that make them easy to use. The camera's small dimensions and eccentric lens locations plus the compact ring light 72 permits integration of the assembly with the slit beam or second pivoting arm 28. Specifically, the slit-lamp microscope 26 is pushed aside for this photography and the camera's LCD screen 68 is used for viewing. The cold LED lights can be brought in close contact with the patient without harm or discomfort.

In addition to the advantages described above, by using the bracket 52 to connect the camera 64 and ring light 70 many a camera light assembly is created that can have many additional advantages. By attaching a forward extension arm to the cavity opening in the bracket 52 that connects to a template placed in a fixed position in front of the camera light assembly (52, 64 and 70), one can create a photo image that is surrounded by a frame that shows the dimensions (mm or inches) in the photo plane. The light assembly 70 is a battery operated light that can provide uniform illumination under any lighting conditions. This camera light assembly (52, 64 and 70) has many applications including use in various sizes in wound clinics to record photographically the size of wounds or incision to document progress in the healing process. Another application is in an emergency room, dermatology, pathology and the like to document injuries, disease processes or specimens with automatic recording of the dimensions in the photo plane. A final application is that the camera light assembly (52, 64 and 70) combination can be used by police departments for photographing documents such as driver's license, insurance cards, or forensic photos that require size documentation.

Further, by attaching a short rearward extension arm to the cavity in the bracket 84 containing a threaded hole 89, the camera light assembly (52, 64 and 70) can be mounted on a tripod for micro photography. Thus, many advantages and applications are provided by use of the present invention. Thus, at the very least, all of the stated objective have been met.

It will be appreciated by those skilled in the art that other various modifications could be made to the device without departing from the spirit and scope of this invention. All such modifications and changes fall within the scope of the claims and are intended to be covered thereby.

What is claimed is:

1. A slit-lamp photo assembly comprising:
   a pivoting arm removably connected to a vertical column associated with a frame; and
   wherein the pivoting arm supports a plate spindle assembly that supports a camera; wherein the plate spindle assembly comprises a support arm that is connected to a bracket that receives the camera; and wherein a light assembly having a light ring is secured to the bracket to position the light ring around the lens of the camera.

2. The slit-lamp photo assembly of claim 1 wherein the support arm is adjustable and has a horizontal portion and a vertical portion that receives the bracket.

3. The slit-lamp photo assembly of claim 2 wherein the support arm has a plate with a recessed area that receives the horizontal portion of the support arm and wherein the plate rotatably connects to the vertical column.

4. The slit-lamp photo assembly of claim 3 wherein the plate has an opening in the recessed area that aligns with a slot in the horizontal portion of the support arm so that when a fastener is disposed through the opening and slot the support arm slides along the plate.

5. The slit-lamp photo assembly of claim 2 wherein the bracket has a vertical portion that is connected to the support arm and a horizontal portion has a slot so that the camera is adjustably secured to the horizontal portion of the bracket.

6. The slit-lamp photo assembly of claim 1 wherein the light assembly is adjustably secured to the bracket with a dual lock tape system.

7. The slit-lamp photo assembly of claim 1 wherein the light assembly is an LED ring light.

8. The slit-lamp photo assembly of claim 1 wherein the bracket is injection molded.

9. The slit-lamp photo assembly of claim 1 wherein the camera is a digital camera with an LCD screen.

10. The slit-lamp photo assembly of claim 3 further comprises an extension arm received by the spindle base and having two openings that align with a slot in the horizontal portion of the spindle arm such that the arm is able to be adjustably connected to both openings.

11. The slit-lamp photo assembly of claim 1 further comprising a portable LED light with a flexible extension attached to the head support of a platform.

12. A slit-lamp photo assembly comprising:
    a frame attached to a platform that has a head support for a patient;
    a carriage movably connected to the platform and having a vertical column;
    a first pivoting arm rotatably connected to the vertical column and supporting a binocular microscope;
    a second pivoting arm rotatably connected to the vertical column and supporting a vertically oriented light source that provides an adjustable slit beam; and
    a third pivoting arm secured to the vertical column and removably and rotatably connected to the vertical column and supporting a plate spindle assembly that supports a camera such that examination of a patient's eye is accomplished with the camera while the microscope is placed aside.

13. A camera light assembly comprising:
    a bracket having a vertical portion and a horizontal portion,
    a camera having a lens adjustably secured to the horizontal portion of the bracket; and
    a light assembly having a ring light surrounding an opening adjustably secured to the bracket adjacent the camera such that the ring light surrounds the lens of the camera; and wherein the ring light forms a Purkinje image on the cornea of an eye of a patient.

14. The assembly of claim 13 where the light assembly is adjustably secured to the bracket using dual lock tape.

15. The assembly of claim 13 wherein the light assembly is a battery powered LED ring light.

16. The assembly of claim 13 wherein the bracket is detachably connected to a tripod.

17. The assembly of claim 13 wherein the bracket is detachably connected to a photo template system.

18. The assembly of claim 17 wherein the photo template system comprises an upwardly extending flange that is received within a cavity of the bracket; an extension extending from the flange; and a template extending from the extension that has an opening therein.

19. The assembly of claim 18 wherein surrounding the opening of the template are measurement indicia.

20. The assembly of claim 19 wherein the template system has a clip secured to the extension that biases against the template.

21. A slit-lamp photo assembly comprising:

a vertical column associated with a frame;

a first pivoting arm rotatably connected to the vertical column;

a second pivoting arm rotatably connected to the vertical column;

a third pivoting arm secured to the vertical column such that the third pivoting arm is removably and rotatably connected to the vertical column; and wherein the third pivoting arm supports a plate spindle assembly that supports a camera.

* * * * *